(12) United States Patent
Urban et al.

(10) Patent No.: US 8,434,350 B2
(45) Date of Patent: May 7, 2013

(54) APPARATUS FOR DETERMINING AND/OR MONITORING A PROCESS VARIABLE OF A MEDIUM

(75) Inventors: Martin Urban, Lorrach (DE); Serguej Lopatin, Lorrach (DE); Oliver Schmidt, Hausach (DE)

(73) Assignee: Endress + Hauser GmbH + Co. KG, Maulburg (DE)

( * ) Notice: Subject to any disclaimer, the term of this patent is extended or adjusted under 35 U.S.C. 154(b) by 99 days.

(21) Appl. No.: 13/122,449

(22) PCT Filed: Aug. 12, 2009

(86) PCT No.: PCT/EP2009/060406
§ 371 (c)(1),
(2), (4) Date: Apr. 4, 2011

(87) PCT Pub. No.: WO2010/040582
PCT Pub. Date: Apr. 15, 2010

(65) Prior Publication Data
US 2011/0179860 A1   Jul. 28, 2011

(30) Foreign Application Priority Data
Oct. 7, 2008 (DE) .......................... 10 2008 050 266

(51) Int. Cl.
*G01N 9/00* (2006.01)
(52) U.S. Cl.
USPC .......................... 73/32 A; 73/54.41; 73/290 V
(58) Field of Classification Search .......................... None
See application file for complete search history.

(56) References Cited

U.S. PATENT DOCUMENTS

| | | | |
|---|---|---|---|
| 4,561,286 A * | 12/1985 | Sekler et al. | 73/24.06 |
| 4,734,609 A | 3/1988 | Jasmine | |
| 4,783,987 A | 11/1988 | Hager | |
| 4,895,017 A * | 1/1990 | Pyke et al. | 73/24.06 |
| 5,852,229 A | 12/1998 | Josse | |

FOREIGN PATENT DOCUMENTS

| | | |
|---|---|---|
| DE | 197 20 519 A1 | 11/1998 |
| DE | 10 2005 036 872 A1 | 2/2007 |
| FR | 2 572 519 | 5/1986 |

OTHER PUBLICATIONS

German Search Report.
International Search Report.

* cited by examiner

*Primary Examiner* — Robert R Raevis
(74) *Attorney, Agent, or Firm* — Bacon & Thomas, PLLC

(57) ABSTRACT

An apparatus for determining and/or monitoring at least one process variable of a medium. The apparatus includes: at least one mechanically oscillatable unit; at least one transducer unit, which excites the mechanically oscillatable unit to mechanical oscillations based on an exciter signal and which receives the mechanical oscillations of the mechanically oscillatable unit and converts such to a received signal. The transducer unit has at least one piezoelectric element. The apparatus further includes: at least one electronics unit, which supplies the transducer unit with the exciter signal and which receives the received signal from the transducer unit; and at least one compensation element, which supplies the exciter signal to the electronics unit and from which the electronics unit receives a compensation signal. The invention provides that the compensation element has at least one at least element made at least partially of a piezoelectric material.

9 Claims, 4 Drawing Sheets

US 8,434,350 B2

APPARATUS FOR DETERMINING AND/OR MONITORING A PROCESS VARIABLE OF A MEDIUM

TECHNICAL FIELD

The invention relates to an apparatus for determining and/or monitoring at least one process variable of a medium. The apparatus includes: at least one mechanically oscillatable unit; and at least one transducer unit, which excites the mechanically oscillatable unit to mechanical oscillations based on an exciter signal and which receives the mechanical oscillations of the mechanically oscillatable unit and converts such to a received signal. The transducer unit includes at least one piezoelectric element; at least one electronics unit, which supplies the transducer unit with the exciter signal and which receives the received signal of the transducer unit; and at least one compensation element, which supplies the electronics unit with the exciter signal and from which the electronics unit receives a compensation signal. The process variable can be, for example, the fill level, density or viscosity of a medium in a container. The medium is, for example, a liquid or a bulk good.

BACKGROUND DISCUSSION

In the state of the art, so-called oscillatory forks are known, with which the fill level of a medium in a container can be monitored. In such case, a mechanically oscillatable unit in the form an oscillatory fork is excited to resonant oscillations by a piezoelectric transducer element. For example, two part piezo drivers with at least one transmitting and one receiver piezo (e.g. DE 39 31 453 C1) or one-piece piezo drivers with only one piezoelectric element (e.g. DE 197 20 519 A1) serves for oscillation excitement or reception.

In the case of the one piezo technology, one piezo element serves both as transmitter and receiver, i.e. the piezo, via which the mechanical system is excited to its resonance frequency also senses the oscillations of the mechanical system. The exciter signal, with which the piezo is supplied, is, in such a case, for example, a rectangular electrical alternating voltage. On the edges of the rectangular signal, the polarity of the piezo capacitance is reversed, whereby charging- and discharging electrical currents arise. Additionally, an electrical current corresponding to the mechanical movements flows during the pulses. The resulting electrical current can be converted to a voltage via a measuring resistor and evaluated.

Since the charging- and discharging electrical currents of the piezo capacitance contain no information concerning the mechanical oscillation, there are undesired side effects, which are suppressed in the state of the art (see DE 197 20 519 A1), for example, by means of a reference capacitor. This happens e.g. in a measuring bridge in which a compensation capacitor is calibrated so that it corresponds to the piezo capacitance. If during operation, i.e. while measuring, the transducer element—i.e. the piezo capacitor and the compensation capacitor are supplied with the same exciter signal, in the case of equal capacitance, equal behavior in the sensed voltage is shown in both by the capacitive fractions in reference to the reverse charging events, or the reverse charging peaks (or the reverse charging electrical currents). The voltage sensed from the transducer unit comes from the received signal, which, thus involves both the charging/discharge curves and the actual wanted signal representing the mechanical oscillations of the oscillatable unit. If the two capacitor voltages are subtracted from one another (or also added in the case of a preceding inversion), then from the received signal there remains only the actual wanted signal, which carries information concerning the mechanical oscillations of the mechanically oscillatable unit (here the oscillatory fork.).

A problem exists in the case of the application of a compensation capacitor in that such shows a different aging and also temperature behavior than the piezoelectric transducer element. Most often, materials are used for capacitors, which have a relatively low temperature coefficient of the dielectric constant. In contrast therewith, for example, piezo materials based on LZT (lead zirconate titanate) possess a very high temperature coefficient of the dielectric constant. Thus there is a clearly different temperature behavior of the respective capacitances. The dielectric properties of LZT materials also change with time (aging). Therefore, a detuning of the compensation can occur both via temperature and also via time, in the state of the art.

SUMMARY OF THE INVENTION

Consequently, an object of the invention is to improve the compensation of the state of the art in reference to temperature stability and preferably also in reference to aging effects of the piezo material.

This object is achieved according to the invention by the feature that the compensation element has at least one element made at least partially of a piezoelectric material. In an embodiment, the compensation element is identical to the element made at least partially of a piezoelectric material, e.g. a polarized or unpolarized or depolarized piezoceramic.

Thus, in contrast to the state of the art, no capacitor is used for compensation in the invention. According to the invention, an element serves for the compensation, which is made preferably at least partially of the same material as the piezoelectric element of the transducer unit. This has the advantage that the temperature coefficients of the dielectric constants are almost identical and, thus, the compensation remains stable with temperature. Also, the two elements are subject to similar aging processes. Additionally, the element of the compensation element made of at least partially of a piezoelectric material, can, in the case of a corresponding mechanical decoupling, for example, be integrated in the transducer element, so that the two elements are not only exposed to the same temperature influences, but are also identically contacted. For this case, in given cases, special embodiments are still required, in order that the compensation element does not register the movements of the mechanically oscillatable unit and produce a signal dependent thereon.

An embodiment includes that the transducer unit has exactly one piezoelectric element. The transducer unit, thus, consists of only one piezoelectric element which serves for both oscillation production as well as detection.

An embodiment provides that the compensation element has exactly one element made at least partially of a piezoelectric material. The compensation element is, thus, in this embodiment, made, for example, from a polarized or depolarized or unpolarized ceramic of a piezoelectric material, for example, LZT based or with barium titanate.

An embodiment provides that the element of the compensation element made at least partially of a piezoelectric material has essentially the same dielectric material properties as the piezoelectric element of the transducer unit. In an additional embodiment, the same geometric dimensions are provided in each case. In an alternative embodiment thereto, i.e. in the case, in which the dimensions of the element of the compensation element made at least partially of a piezoelectric material and the dimensions of the piezoelectric element of the transducer unit are different, the signals are correspondingly differently weighted, or amplified. Especially, both piezoelectric elements come furthermore preferably from the same manufacturing lot. The element of the compensation element and the element of the transducer unit have, thus, in this embodiment, essentially the same relevant material properties and in an additional embodiment also the same relevant dimensions, i.e. they behave and age essentially equally.

An embodiment provides that the element of the compensation element made at least partially of a piezoelectric material is essentially depolarized or unpolarized. In this embodiment, a supplying of the exciter signal to the compensation element leads to no mechanical oscillations of the element of the compensation element made at least partially of a piezoelectric material, or no electrical signals/voltages are produced in the compensation element by the mechanical oscillations. Through the application of a depolarized, or unpolarized or an essentially polarization free compensation element, an almost equal behavior is shown in reference to aging and temperature dependence, so that a stable compensation of the reverse charging electrical currents occurs.

An embodiment includes that the element of the compensation element made at least partially of a piezoelectric material and the mechanically oscillatable unit are essentially mechanically decoupled from one another. Since this embodiment cancels a mechanical coupling/contact of the mechanically oscillatable unit and the compensation element, which is in principle, through its piezoelectric properties, susceptible/sensitive to mechanical oscillation or also oscillatable, i.e. given a decoupling, the electrical signal of the compensation element bears no information concerning the oscillations of the oscillatable unit, but instead essentially only the charging/discharge curve characterized by its capacitance. In this embodiment, thus, the piezoelectric element of the compensation element can be either polarized or unpolarized. In an additional embodiment, the compensation element is embodied in such a manner and arranged relative to the mechanically oscillatable unit that the orientation of the polarization of the compensation element effects a decoupling relative to the mechanically oscillatable unit. For example, the polarization is parallel to the membrane, or diaphragm, of the mechanically oscillatable unit, to which the compensation element is secured.

An embodiment provides that the element of the compensation element made at least partially of a piezoelectric material is embodied in such a manner and is mechanically coupled with the mechanically oscillatable unit, that electrical signals, which are produced by mechanical forces by the mechanically oscillatable unit acting on the element of the compensation element made at least partially of a piezoelectric material, essentially cancel one another. In this embodiment, thus, the mechanical oscillations produce electrical signals in the piezoelectric element. However, these signals cancel one another, so that the resultant signal of the compensation element is free of effects of the mechanical oscillations or forces. In this embodiment, thus, special value is placed on a suitable placing of the element of the compensation element made at least partially of a piezoelectric material. In the case of a membrane, or diaphragm, oscillator, this can be implemented in such a manner, for example, that the piezoelectric element applied for the compensation is so emplaced on the inner side of the membrane, or diaphragm, as a mechanically oscillatable unit, that its outer surface is essentially symmetrically divided in the middle by a nodal region (neutral line). This is true for oscillations of the second mode. Therewith, electrical signals arising from the oscillations in the piezoelectric element of the compensation element are compensated. Consequently, only the charging/discharge curves characteristic of the piezo capacitance occur. This has the advantage that the piezoelectric element of the compensation element can be, or remain, polarized, and it is additionally exposed to the same loadings as the piezoelectric element of the transducer unit. Thus temperature and aging act in the same measure on the compensation element as on the transducer unit.

An embodiment includes that the mechanically oscillatable unit is an oscillatable membrane, or diaphragm, or a single rod or an oscillatory fork.

An embodiment provides that the process variables are fill level, viscosity or density of a medium in a container.

BRIEF DESCRIPTION OF THE DRAWINGS

The invention will now be explained in greater detail based on the appended drawing, the figures of which show as follows.

DETAILED DISCUSSION IN CONJUNCTION WITH THE DRAWINGS

Figure 1:
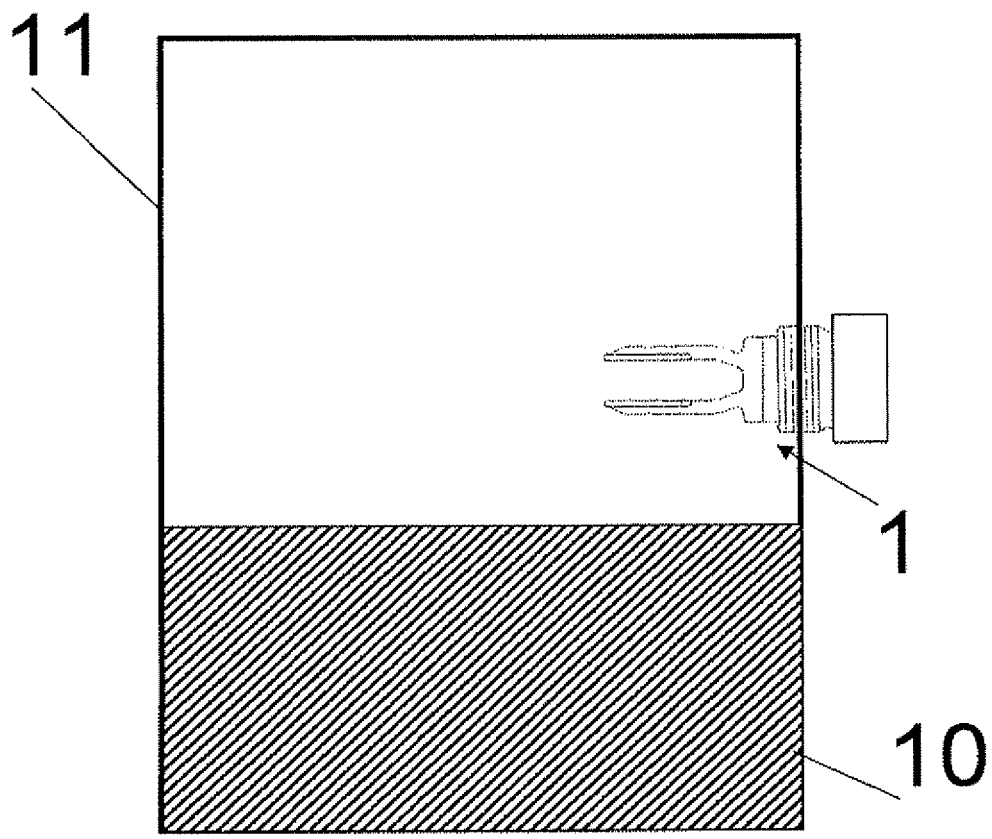
FIG. 1 is a schematic example of application of a measuring device of the invention.

FIG. 1 shows, schematically, monitoring of the fill level of a medium 10 in a container 11 by means of a measuring device of the invention. The mechanically oscillatable unit 1 is here embodied as an oscillatory fork, wherein the two fork tines are secured to a membrane, or diaphragm. The oscillations of the mechanically oscillatable unit 1 are dependent on contact with the medium and, thus, on the degree of the covering by the medium, or on its fill level, however, also on the properties of the medium such as density or viscosity. These process variables can be ascertained correspondingly from the characterizing variables of the oscillations such as frequency, amplitude or phase relative to an exciter signal or changes can be indicated therewith.

The mechanically oscillatable unit 1 is mechanically coupled to a transducer unit, which excites the mechanically oscillatable unit 1 to mechanical oscillations based on an electrical exciter signal and which, conversely, receives the mechanical oscillations of the mechanically oscillatable unit 1 and converts such to an electrical received signal. The signals are most often electrically alternating, voltage signals. The exciter signal is, for example, a rectangular signal.

In the state of the art it is usual, for example, that the transducer unit is composed of two piezoelectric elements or one piezoelectric element. In the first case the tasks of transmitting and receiving the signals are carried by two units. In the second case, both the oscillation production as well as also the oscillation detection is performed by one piezoelectric element. This leads to the fact that the capacitive properties of the piezoelectric element affect the received signal. At the edges of the exciter signal it reverse charging phenomena of the piezoelectric element arise, as represented in the received signal in the form of charging- and discharging curves. These curves are superimposed on the actual wanted signal, the carrier of the information concerning the oscillations of the mechanically oscillatable unit, and are dependent only on the electrical properties of the piezoelectric element. Therefore, it is advantageous to mask out these curves and work only with the pure oscillatory signal.

Figure 2:
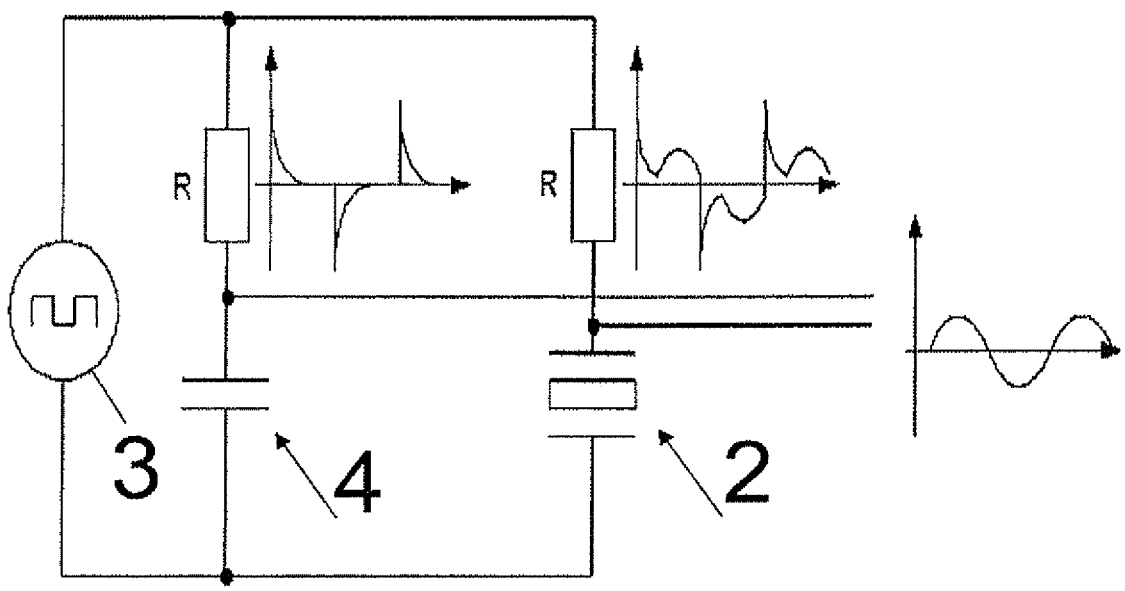
FIG. 2 is a circuit for compensation of the charging/discharge curves according to the state of the art.

FIG. 2 shows a circuit of the state of the art, in which the charging and discharging curves are eliminated.

A capacitor as compensation element 4 is provided here in parallel with the piezoelectric element of the transducer unit 2. The electronics unit 3 supplies the transducer unit 2 and the compensation element 4 with the same exciter signal, e.g. a rectangular signal.

Alongside the resistors R, the respective tappable voltage signals are presented in FIG. 2. As is easily seen, the voltage signal of the compensation element 4 shows only the typical charging or discharging behavior of a capacitor. In the voltage curve above the transducer unit 2, the superposition of the actual sinusoidal oscillation signal of the mechanically oscillatable unit with the charging and discharging curves is evident. If the capacitor of the compensation element 4 has the same capacitance as the piezoelectric element of the transducer unit 2, the two have the same charging and discharging curves. Therefore, a difference of the two signals leaves only the actual wanted signal in the form of the sinusoidal signal dependent on the oscillations of the mechanically oscillatable unit. This difference is also shown here, to the right of the figure. In an alternative embodiment in the state of the art, both signals are added, after inversion of one of the signals.

The disadvantage of this method in the state of the art is that the capacitances of the transducer unit 2 and the compensation serving capacitor 4 are not always identical. Thus, different aging behaviors and also different temperature dependencies are shown. Therefore, the compensation is reliable only in a certain context.

Figure 3:
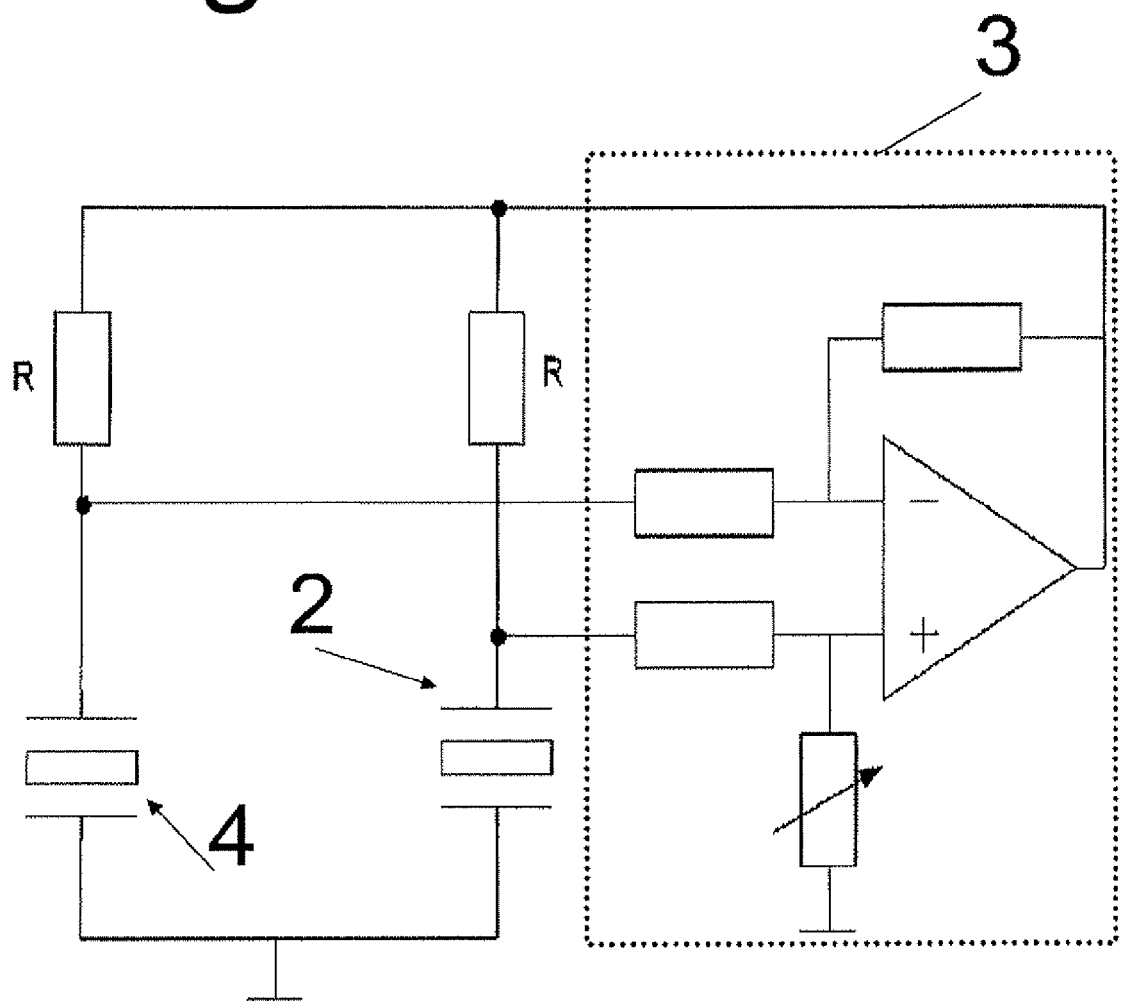
FIG. 3 is a circuit of the invention.

FIG. 3 shows an example of implementing the invention. The compensation element 4 here, like the transducer unit 2, is composed only of one element, which is made of a piezoelectric material. Especially, both elements, the compensation element 4 and the transducer unit 2, are of the same material and are preferably also from the same manufacturing lot. Preferably, the two piezoelectric elements 2, 4 are placed essentially at the same location, i.e. they are exposed to the same environmental temperatures and loadings.

In the electronics unit 3 illustrated here, the tapped voltage signals of both piezoelectric elements 2, 4 are fed to a difference amplifier. The two signals are here, thus, subtracted from one another, so that only the sinusoidal, wanted signal carrying the information concerning the oscillations of the mechanically oscillatable unit, with which the transducer element is mechanically coupled, remains. This signal is then fed to an evaluation (not shown). Furthermore, the signal is amplified as the exciter signal of the transducer unit 2 and fed back to the compensation element 4. In an alternative embodiment, the received signal and the compensation signal are evaluated and processed separately from one another in the electronics unit 3.

Regarding the embodiment and application of the compensation element 4, which in an embodiment is especially composed only of one piezoelectric element, care should be taken that the tappable signal of the compensation element 4, which serves for the compensation, is itself uninfluenced by the mechanical oscillations. I.e. the compensation signal should only carry the charging and discharging curves.

Advantageously, thus, the compensation element is exposed to the same temperature and if possible the same mechanical load as the transducer unit through its embodiment and application. At the same time, however, the signal of the compensation element should be independent of he mechanical oscillations of the mechanically oscillatable unit.

In an embodiment, therefore, the piezoelectric element of the compensation element 4 is depolarized or unpolarized. In an additional embodiment, the compensation element 4 is mechanically decoupled from the mechanically oscillatable unit, e.g. by a corresponding damping element or by an essentially contactless application.

Figure 4A:
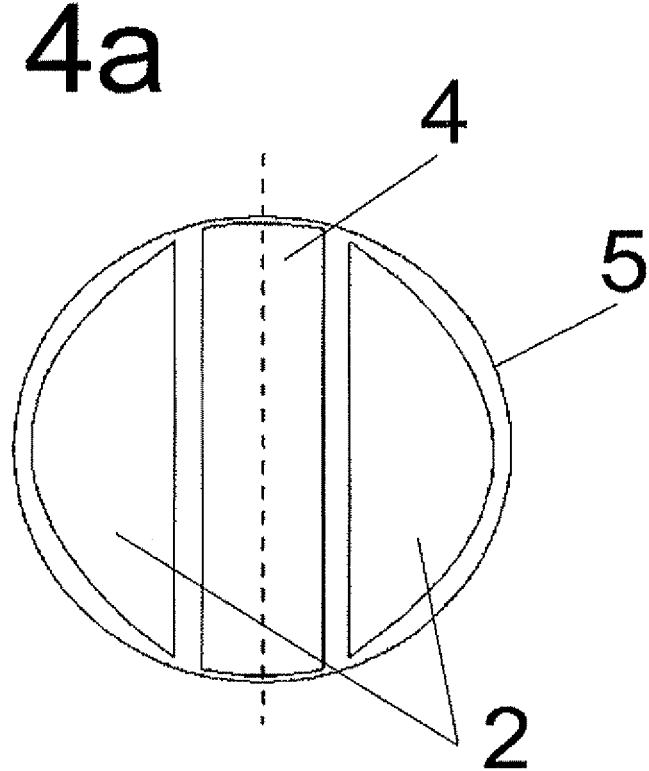
FIGS. 4a, 4b are a plan view of, and a section through, a membrane, or diaphragm, of a measuring device of the invention.
Figure 4B:
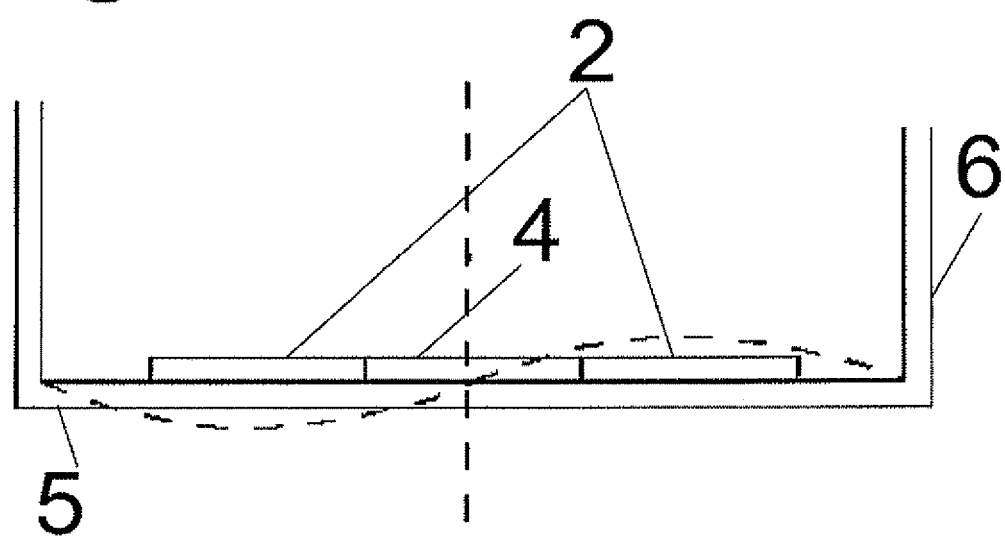

FIGS. 4a and 4b show a third variant.

FIG. 4a shows a plan view of the circular membrane, or diaphragm, 5 of a measuring apparatus according to the invention. The piezoelectric element of the transducer unit 2 is composed of two semicircular surfaces embodied symmetrically to a central axis of the membrane, or diaphragm, 5. The two surface portions serve, in each case, both as producer and receiver of the mechanical oscillations. The compensation element 4, embodied as a piezoelectric element, is arranged centrally between these surface portions. The piezoelectric element 4 is rectangularly shaped, with the narrow sides being rounded to match the membrane, or diaphragm, 5. The compensation element 4 is itself arranged and embodied symmetrically to the dashed central axis of the membrane, or diaphragm, 5. In this nodal region, thus, the compensation element 4 is quasi 'divided' along this neutral line into two exactly equally large elements. This has the advantage that the effects of the oscillations of the mechanically oscillatable unit on the compensation element 4 are compensated oppositely in the case in which the mechanically oscillatable unit executes second mode oscillations. The embodiment and application of the compensation element 4 thus depend on which oscillatory mode is excited.

FIG. 4b shows a section through the housing 6 and the membrane, or diaphragm, 5. The central perpendicular of the membrane, or diaphragm, 5 is entered dashed, which thus, is perpendicular to the central axis of the membrane, or diaphragm, 5 drawn in FIG. 4a. Furthermore, an oscillatory movement of the membrane, or diaphragm, 5 is drawn dashed and strongly enlarged. As is easily seen, half of the compensation element 4 experiences a movement inwardly and the other half a movement outwardly, i.e. the voltages produced by the mechanical movement in the compensation element 4 are essentially oppositely compensated, i.e. they exactly cancel one another, so that the tappable voltage signal of the compensation element 4 is independent of the mechanical oscillations.

The piezoelectric element of the compensation element 4 and the piezoelectric element of the transducer unit 2 are located in a plane and the two are in near contact with the medium via the membrane, or diaphragm, 5.

The mechanically oscillatable unit is, by way of example, here, only a membrane, or diaphragm, placed on the housing 6 in sealing relationship on one end, i.e. this is a so-called membrane, or diaphragm, oscillator.

The invention claimed is:
1. An apparatus for determining and/or monitoring at least one process variable of a medium, comprising:
  at least one mechanically oscillatable unit;
  at least one transducer unit; which excites said mechanically oscillatable unit to mechanical oscillations via an exciter signal and which receives the mechanical oscillations of said mechanically oscillatable unit and converts such to a received signal; and
  at least one electronics unit, which supplies at least one compensation element with the exciter signal and from which said electronics unit receives a compensation signal, wherein:
  said transducer unit has at least one piezoelectric element, and the at least said one electronics unit, supplies said transducer unit with the exciter signal and which receives the received signal from said transducer unit;

said compensation element has at least one element made at least partially of a piezoelectric material and said mechanically oscillatable unit is an oscillatable membrane, or diaphragm, or a single rod or an oscillatory fork.

2. The apparatus as claimed in claim 1, wherein:
said transducer unit has exactly one piezoelectric element.

3. The apparatus as claimed in claim 1, wherein:
said compensation element has exactly one element made at least partially of a piezoelectric material.

4. The apparatus as claimed in claim 1, wherein:
said element of said compensation element made at least partially of a piezoelectric material has essentially the same dielectric material properties as said piezoelectric element of said transducer unit.

5. The apparatus as claimed in claim 1, wherein:
said piezoelectric element of the transducer unit and said element of said compensation element made at least partially of a piezoelectric material are made essentially of the same piezoelectric material.

6. The apparatus as claimed in claim 1, wherein:
said element of said compensation element made at least partially of a piezoelectric material is essentially depolarized or unpolarized.

7. The apparatus as claimed in claim 1, wherein:
said element of said compensation element made at least partially of a piezoelectric material and said mechanically oscillatable unit are essentially mechanically decoupled from one another.

8. The apparatus as claimed in claim 1, wherein:
said element of said compensation element made at least partially of a piezoelectric material is embodied in such a manner and is coupled mechanically to said mechanically oscillatable unit in such a manner, that electrical signals produced by mechanical forces by said mechanically oscillatable unit acting on said element of said compensation element made at least partially of a piezoelectric material are essentially oppositely compensated.

9. The apparatus as claimed in claim 1, wherein:
the process variable is fill level, viscosity or density of a medium in a container.

* * * * *